(12) United States Patent
Howes

(10) Patent No.: US 9,438,773 B2
(45) Date of Patent: Sep. 6, 2016

(54) UNIVERSAL DUAL CAMERA ADAPTER

(75) Inventor: Allen R. Howes, Danville, CA (US)

(73) Assignee: Transamerican Technologies International, San Ramon, CA (US)

(*) Notice: Subject to any disclaimer, the term of this patent is extended or adjusted under 35 U.S.C. 154(b) by 854 days.

(21) Appl. No.: 13/590,604

(22) Filed: Aug. 21, 2012

(65) Prior Publication Data

US 2013/0100271 A1    Apr. 25, 2013

Related U.S. Application Data

(60) Provisional application No. 61/550,236, filed on Oct. 21, 2011.

(51) Int. Cl.
| | |
|---|---|
| H04N 9/47 | (2006.01) |
| H04N 7/18 | (2006.01) |
| H04N 5/225 | (2006.01) |
| A61B 3/135 | (2006.01) |
| G02B 21/00 | (2006.01) |
| G02B 21/36 | (2006.01) |
| A61B 3/14 | (2006.01) |

(52) U.S. Cl.
CPC ............ *H04N 5/2251* (2013.01); *A61B 3/135* (2013.01); *G02B 21/0012* (2013.01); *G02B 21/362* (2013.01); *A61B 3/145* (2013.01); *G02B 21/365* (2013.01); *G02B 21/367* (2013.01)

(58) Field of Classification Search
CPC ............................ G02B 21/365; G02B 21/367
USPC ...................................... 348/78, 79; 359/368
See application file for complete search history.

(56) References Cited

U.S. PATENT DOCUMENTS

| | | | |
|---|---|---|---|
| 3,820,882 | A | 6/1974 | Jakubowski |
| 4,143,938 | A | 3/1979 | Feinbloom |
| 4,148,072 | A | 4/1979 | Vockenhuber |
| 4,272,161 | A | 6/1981 | Feinbloom |
| 4,300,167 | A | 11/1981 | Miller et al. |
| 4,344,667 | A | 8/1982 | Wooff, Jr. |
| 4,688,907 | A | 8/1987 | Kleinberg |
| 4,781,448 | A | 11/1988 | Chatenever et al. |
| 4,805,027 | A | 2/1989 | Sluyter |
| 5,264,928 | A | 11/1993 | Howes |
| 5,528,426 | A | 6/1996 | Howes |
| 5,568,188 | A | 10/1996 | Widmer et al. |

(Continued)

FOREIGN PATENT DOCUMENTS

WO        99/30198 A1    6/1999

*Primary Examiner* — Jefferey Harold
*Assistant Examiner* — Omer Khalid
(74) *Attorney, Agent, or Firm* — Haynes Beffel & Wolfeld LLP

(57) ABSTRACT

A universal adapter system having a video camera mount and a digital camera mount for attaching a video camera and a digital camera to a single port of an optical observation device, such as a standard microscope, that allows for simultaneous video and digital camera imaging. An example digital camera mount includes a C-clamp attachment for attaching a standard, off-the-shelf digital camera and a sleeve attached to the adapter housing that allows use of an extendable zoom lens of the digital camera. The adapter may provide increased capabilities by use of a rotatable portion to allow positioning of the digital camera relative to the optical observation device, a parfocal zoom lens for simultaneous zoom adjustment of video and digital cameras, an auxiliary zoom lens, a fine focus adjustment for adjusting the video image independent of the digital image, a smartphone adapter, a Toric reticule and a light filter.

36 Claims, 15 Drawing Sheets

(56) References Cited

U.S. PATENT DOCUMENTS

| | | | | |
|---|---|---|---|---|
| 6,020,993 | A * | 2/2000 | Greenberg | G02B 21/361 359/363 |
| 6,113,533 | A | 9/2000 | Howes et al. | |
| 6,996,341 | B2 | 2/2006 | Hanzawa | |
| 7,753,600 | B2 * | 7/2010 | Gartner | G02B 21/362 396/419 |
| 2003/0179445 | A1 * | 9/2003 | Maenle | G01N 1/30 359/368 |
| 2004/0091259 | A1 * | 5/2004 | Hanzawa | G03B 35/10 396/534 |
| 2012/0275019 | A1 * | 11/2012 | Letovsky | G02B 21/06 359/385 |
| 2013/0070251 | A1 * | 3/2013 | Das | G03H 1/0443 356/457 |
| 2013/0258462 | A1 * | 10/2013 | May | G02B 21/22 359/464 |
| 2014/0026683 | A1 * | 1/2014 | Hayworth | G01N 1/06 73/863.01 |
| 2014/0071263 | A1 * | 3/2014 | Laguarta Bertran | G02B 21/0016 348/79 |

* cited by examiner

UNIVERSAL DUAL CAMERA ADAPTER

CROSS-REFERENCES TO RELATED APPLICATIONS

The present application is a non-provisional of, and claims the benefit of U.S. Provisional Patent Application No. 61/550,236, filed Oct. 21, 2011, the entire contents of which are incorporated herein by reference.

The following commonly-assigned application and patent discloses related subject matter, and is incorporated herein by reference in its entirety: U.S. Pat. No. 5,264,928 entitled, "Universal Adapter for Mounting Cameras to Microscopes" filed on Jun. 29, 1992.

BACKGROUND OF THE INVENTION

1. Field of the Invention

The present invention relates generally to optical equipment, and more particularly to an adapter assembly suitable for mounting a video camera and a digital camera, to a surgical microscope.

Medical and research microscopes frequently include a port to allow attachment of a video system, a still image camera (such as a digital SLR camera), or the like. In order to permit the attachment of more than one camera to a single optical port, dual camera adapters are also available.

While functional, such conventional video adapters generally possess lenses which provide only a single focal length for the video camera or other cameras attached to such adapters. Additionally, existing adapters are not typically suitable for use with off-the-shelf digital cameras and do not allow full use of the zoom feature of such a digital camera. Furthermore, many such adapters are capable of being mounted only on a particular brand of microscope. Thus, a hospital or laboratory must possess numerous specific adapters in order to handle the various combinations of video cameras, cameras, and brand of microscope employed.

Of particular concern is the desire to provide different relative magnification for the video camera and the digital camera. With present equipment, such a change in relative magnification may require that the entire video adapter be removed and replaced with a second video adapter in order to provide for the focal lengths for each camera.

For these reasons, it would desirable to provide a universal adapter that allows for simultaneous imaging with a standard digital camera and video camera using a single port, ideally leaving the remaining optical port available for auxiliary use. It would be preferable for such a universal adapter to be capable of receiving a variety of different video cameras and off-the-shelf commercially available digital cameras for use on different brands of microscope beam splitters. Such universal adapter systems should further provide for a wide range of different focal length magnifications for both the attached video camera and the attached digital camera. It would also be desirable to provide an adapter that allows for simultaneous adjustment of focus and magnification during simultaneous digital and video imaging, while also allowing focus and/or magnification adjustment of the imaging devices independent from one another.

2. Description of the Background Art

Adapters for simultaneously mounting a video camera and a 35-mm camera on one side of a surgical microscope beam splitter are shown in U.S. Pat. Nos. 4,272,161 and 4,143,938. Such adapters are commercially available from Carl Zeiss, Inc., and manufactured by Urban Engineering Co., Burbank, Calif. Beam Splitters having integral video cameras are shown in U.S. Pat. Nos. 4,805,027 and 4,344,667. A beam splitter having three identical optical trains and four viewing stations is shown in U.S. Pat. No. 4,688,907. Automatic iris control systems for use with surgical microscope adapters are shown in U.S. Pat. Nos. 3,820,882 and 4,300,167. A zoom lens adapter for an endoscopic camera is shown in U.S. Pat. No. 4,781,448.

BRIEF SUMMARY OF THE INVENTION

The present invention overcomes the limitations described above by providing a universal adapter for connecting a video camera and a standard digital camera for simultaneous imaging using a single optical port of a microscope or imaging device. Embodiments of the video/camera connectors can include a zoom system to provide different relative magnification for the video camera and the digital camera without having to resort to removing the entire video adapter and replacing it with a second video adapter to provide the desired focal length for each camera. Instead, such embodiments of the present adapters may possess lenses which provide associated focal lengths for each of the video port and the camera port. Embodiments of the adapters may also be particularly suitable for use with off-the-shelf digital cameras, and/or include digital camera ports which accommodate movement of the types of zoom lenses often included with such cameras so as to allow full use of the zoom feature of a digital camera. Example embodiments of the adapters have input and/or output ports suitable for coupling with a wide variety of brands of video cameras, digital image cameras, and surgical microscopes employed in a medical setting.

In accordance with some embodiments, the universal adapter comprises a main body including a housing and an internal beam splitter oriented to receive light along an axial input image path from a conventional beam splitter of an optical observation device, such as a surgical microscope or an ophthalmic slit lamp. The main body housing includes an axial passageway having a proximal and distal end and an optical device mount near the proximal end configured to attach the adapter to the optical device, preferably to a single optical port. The adapter further comprises a video camera mount and a digital camera mount configured to attach a standard video camera and a standard, off-the-shelf digital camera to the main body housing so as to facilitate simultaneous imaging with the cameras. The adapter beam splitter reflects a portion of the light from the input image path along a transverse beam path, typically along a first optical path to a video camera mount and a second optical path to a digital camera mount of the adapter.

In a particular aspect of the present invention, the video camera mount is attached to the main body housing along the first optical path (typically transverse to the input image path entering the main housing body from the optical device). The video camera mount comprises a C-type mount ring and the like (e.g. bayonet type or custom mounts), where the mount ring may be detachably secured within the video mount to permit attachment of virtually any type of video camera. The video camera mount (or alternatively the main body) may further include a auxiliary zoom lens and/or a fine focus adjustment disposed along the first optical path to allow for image adjustment of the video image independent of the digital camera image.

In another aspect, the digital camera mount attaches to the main body housing near the distal end along the second optical path to align the digital camera with the second optical path. The digital camera mount includes a sleeve that allows extension of an objective zoom lens of the digital camera therethrough and an attachment means, such as a C-clamp, for securing the digital camera to the sleeve along the second optical path. Preferably, the C-clamp includes a mounting screw for interfacing with a tripod mount of the digital camera and is dimensioned so as to secure any of a variety of differing types and brands of digital cameras. The digital camera mount and/or the main body housing may further include a centering mechanism, such as a plurality of inwardly extending centering screws, which allows a user to center the digital camera mount along the second optical path.

In another aspect, the main body housing includes a rotatable portion near the distal end, the rotatable portion having a reflective surface for directing the second optical path along a direction transverse to the input image path from the optical observation device. This rotatable portion allows the mounted digital camera to be adjusted to a position suitable for operation by a primary user of the optical observation device.

In an embodiment, the digital camera mount can be attached to the binocular tube of a surgical microscope or ophthalmic slit lamp. The adapter may include a light filter that acts as a barrier to light of a particular wavelength or range of wavelengths (e.g. a yellow filter of wavelengths allowing transmission of wavelengths of about 525 nm). Such a filter can be used to in conjunction with fluorescein dye on the cornea that is excited by cobalt blue light which enhances visibility of corneal defects or disease to allow for improved visibility and documentation of defects or diseases of the cornea. Alternatively, these elements can be used to document contact lens fitting. The adapter may also include a Toric reticule that fits into an eyepiece of the adapter to allow the position of a Toric intraocular lens to be documented to provide more predictable and accurate surgical outcomes. The universal adapter may also include an adapter to allow a smartphone, such as an iPhone™, having a video or still image camera capability to be used with the universal adapter, or alternatively, the smartphone adapter may be used separately to attach a smartphone to a binocular tube of a surgical microscope or ophthalmic slit lamp.

In accordance with some embodiments, the adapter includes a parfocal zoom lens with an adjustable iris aperture near the proximal end of the main body housing so as to allow for simultaneous adjustment of the image for both the video camera and the digital camera. A particular advantage of the invention is that the magnifications of the video camera and digital camera can be adjusted either simultaneously or can be adjusted independent of one another.

DETAILED DESCRIPTION OF THE INVENTION

Figure 1:
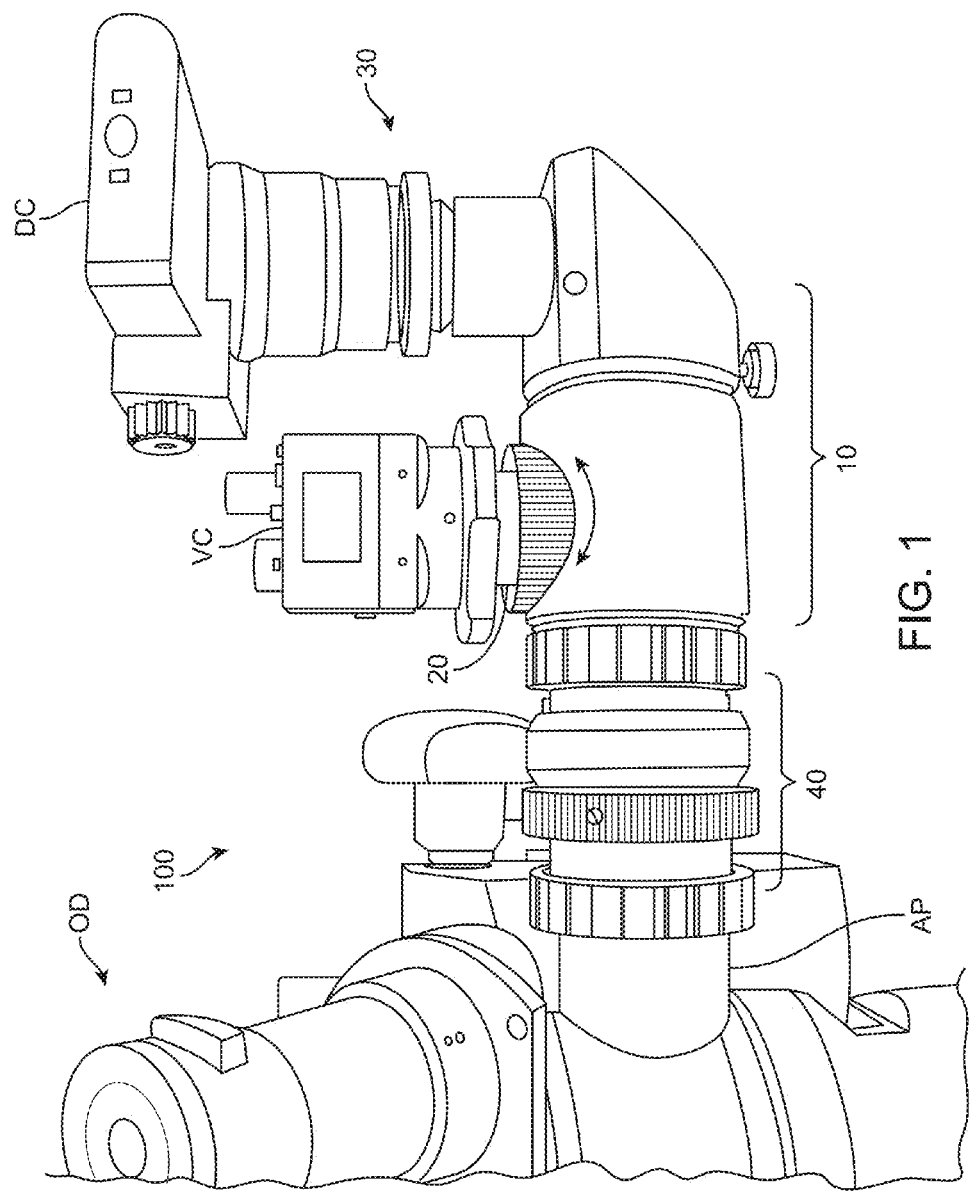
FIG. 1 is a view of an example universal adapter connecting a video camera and digital camera to an optical port of a microscope constructed in accordance with principles of the invention.

As shown in FIG. 1, a universal adapter system 100 may be used to mount a video camera VC and a digital camera DC on a single auxiliary optical port AP of optical observation device OD, in this case, a surgical microscope. The optical observation device OD may include an optical imaging device such as a surgical microscope, an ophthalmic slit lamp, or the like. Observation device OD includes a beam splitting assembly that directs light received along the optical viewing path to one or more auxiliary optical ports AP, typically two optical ports, one on either side of the optical viewing eyepieces of the optical observation device OD. In an exemplary embodiment, the universal adapter system 100 has a main body housing 10 having a video camera mount 20, a digital camera mount 30, and an optical observation device mount 40. Each of the mounts has an axial passage through which an optical path directed from the optical observation OD passes during imaging. As will be discussed in more detail below, the universal adapter system 100 and each of the main body video camera mount 20 and digital camera mount 30 may include a number of components that permit mounting of differing video cameras and/or digital cameras to allow for the interconnection of a variety of optical observation devices OD from different manufacturers, and which further allows for a number of optical features during simultaneous imaging with a video camera VC and a digital camera DC.

Figure 2:
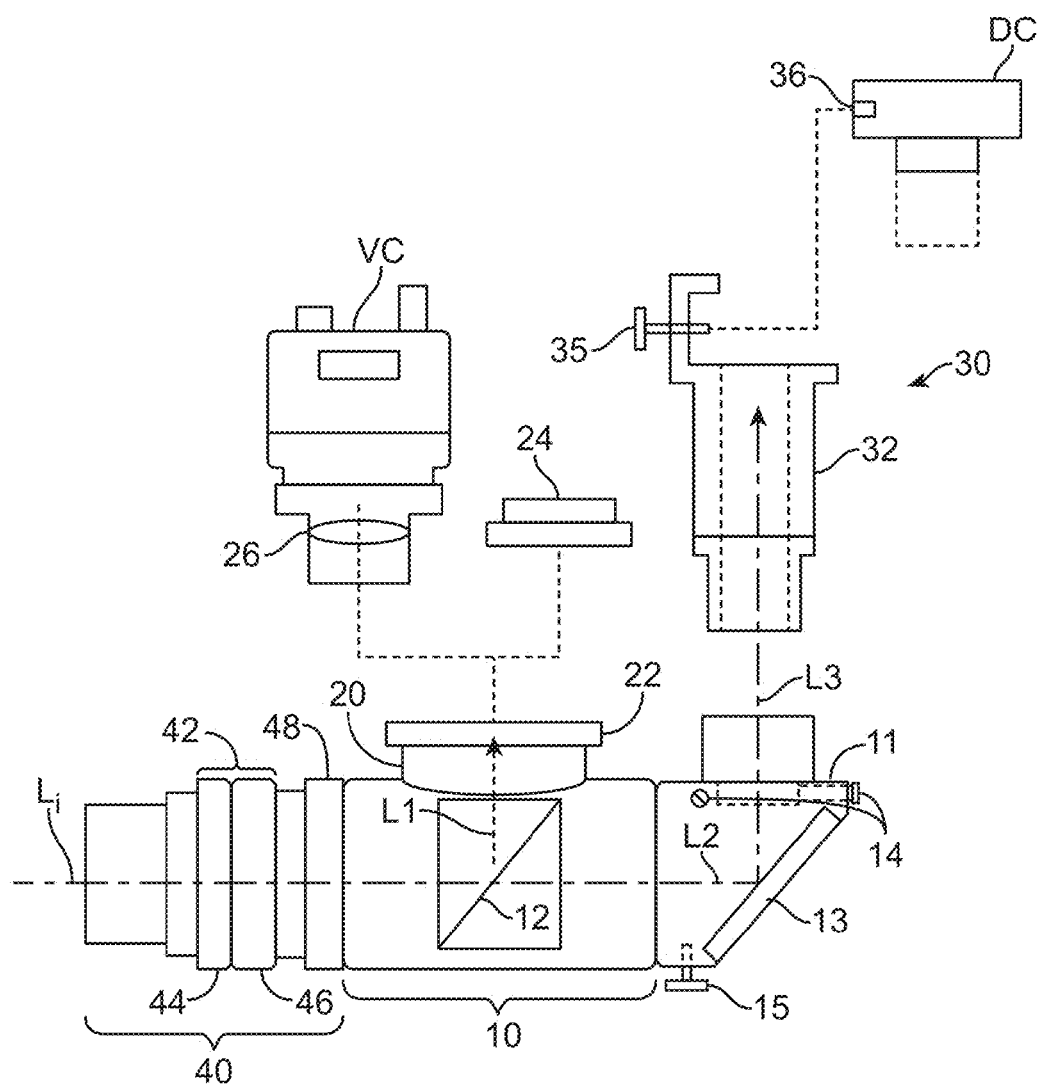
FIG. 2 is a schematic of an example universal adapter system in accordance with embodiments of the invention.

Referring now to FIG. 2, the basic construction of the universal adapter system 100 of the present invention will be described. The essential components of the system 100 include a main body housing 10 having an axial passageway extending therethrough having a proximal and distal end. The main body 10 is generally cylindrical in shape and defines the axial passage through which optical axis Li of the input image path extends when the main body housing 10 is mounted to the optical observation device with the optical mount 40 at the proximal end, which may be secured to the main body housing 10 by an adjustable locking ring 48. The main body housing 10 includes a beam splitter 12 for directing a portion of light from optical path Li to a first optical path L1 for imaging with the video camera VC and to a second optical path L2 for imaging with the digital camera DC. The beam splitter 12 may comprise a pair of opposed prisms, or may utilize a single prism, a partially reflective mirror, a pivotable mirror, or any equivalent structure which could reflect or partially reflect an incident axial beam L1 along a beam path transverse to optical axis Li of the input image path.

In an example embodiment, beam splitter 12 reflects a greater amount of light from optical path Li along optical path L1 than along optical path L2, typically at a proportion within a range from about 60/40 to about 80/20, preferably about 70/30. This configuration facilitates higher quality simultaneous imaging, since the digital camera may require less light than the video camera during imaging. The proportion of light, however, may be equal or inverse to the proportion described above depending on the sensitivity and location of the imaging devices mounted to the adapter.

The proximal end of the main body housing 10 is detachably secured to the optical observation device OD with the optical observation mount 40, typically using a conventional locking ring. The auxiliary optical port AP of the optical observation device OD includes an axial passage, along which optical path Li is directed from a beam splitter internal to the optical observation device OD. In one aspect, the optical mount 40 may include a lens cartridge 42 or parfocal zoom lens assembly removably attached to the main body 10. Any of the optical mount assemblies 40 described herein may be mounted to an optical port of the optical observation device and secured with a locking ring.

In some embodiments, the lens cartridge of the optical observation device mount 40 includes a parfocal zoom lens assembly, which includes a zoom adjustment ring 46 that allows a user to simultaneously adjust the zoom of the optical path during imaging with the video and digital camera. Preferably, the zoom adjustment ring 46 allows for parfocal zoom from 40 to 80 mm. Typically, the parfocal lens assembly is used with an adjustable iris, which may be integrated with the parfocal lens assembly as a single component.

In other embodiments, the optical observation device mount 40 may include lens cartridge that includes multiple interchangeable lenses of differing fixed focal lengths so as to allow a user to adjust the focal length by switching between lenses. For example, a lens cartridge may include multiple interchangeable lenses of fixed focal lengths of F55, F65, F85, F107 and F135, respectively. Typically, the multiple interchangeable lenses are used with a tubular iris assembly that may be integrated with the lens cartridge. The lens cartridge 42 may be attached to the proximal end of the main body housing 10 by a threaded connector received in a threaded receptacle in the proximal end of the main body housing 10. In some embodiments, the multiple interchangeable lenses may be attached or screwed into a proximal end of main body housing 10 along with a tubular iris assembly and surrounded by optical observation device mount 40 which is attached to the main body 10 with locking ring 48.

Figure 3:
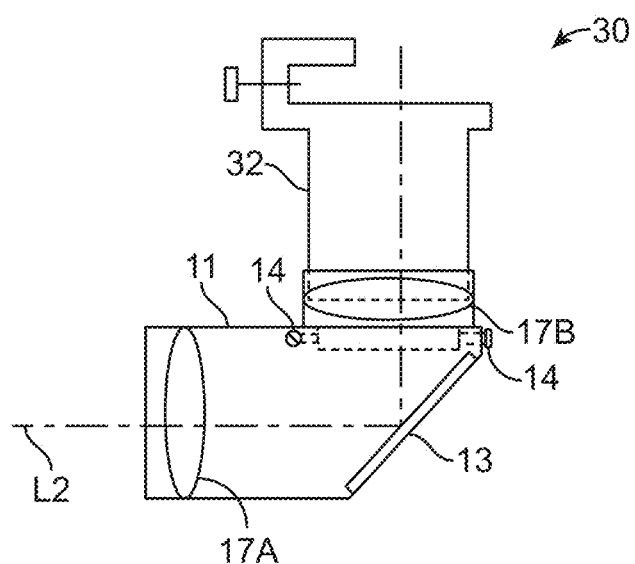
FIG. 3 is a schematic of a rotatable portion of the adapter and a digital camera mount in accordance with embodiments of the invention.
Figure 4:
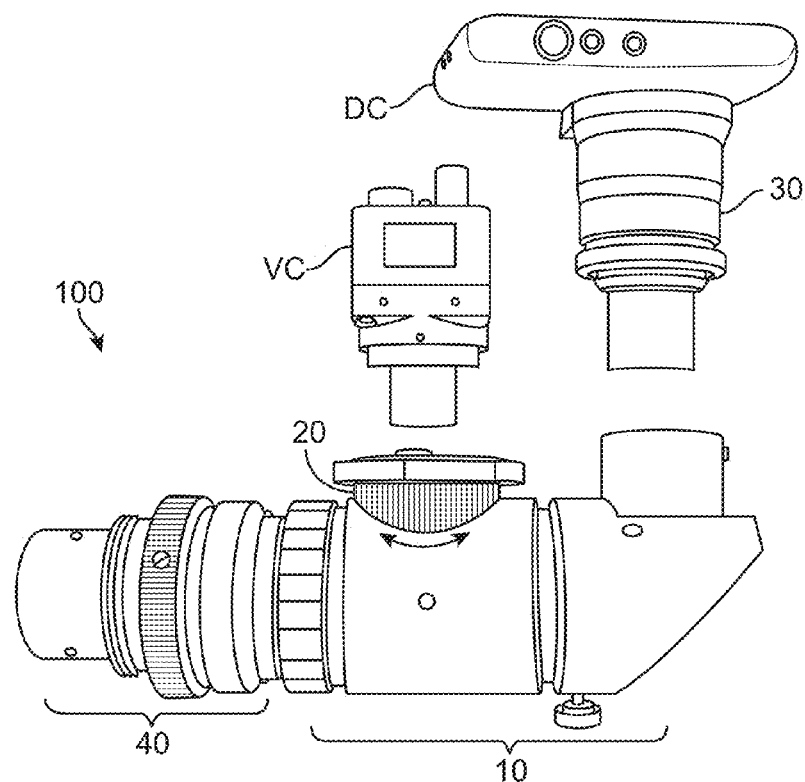
FIGS. 4 and 5 shows an example universal adapter system before and after mounting of the video camera and digital camera, respectively.
Figure 5:
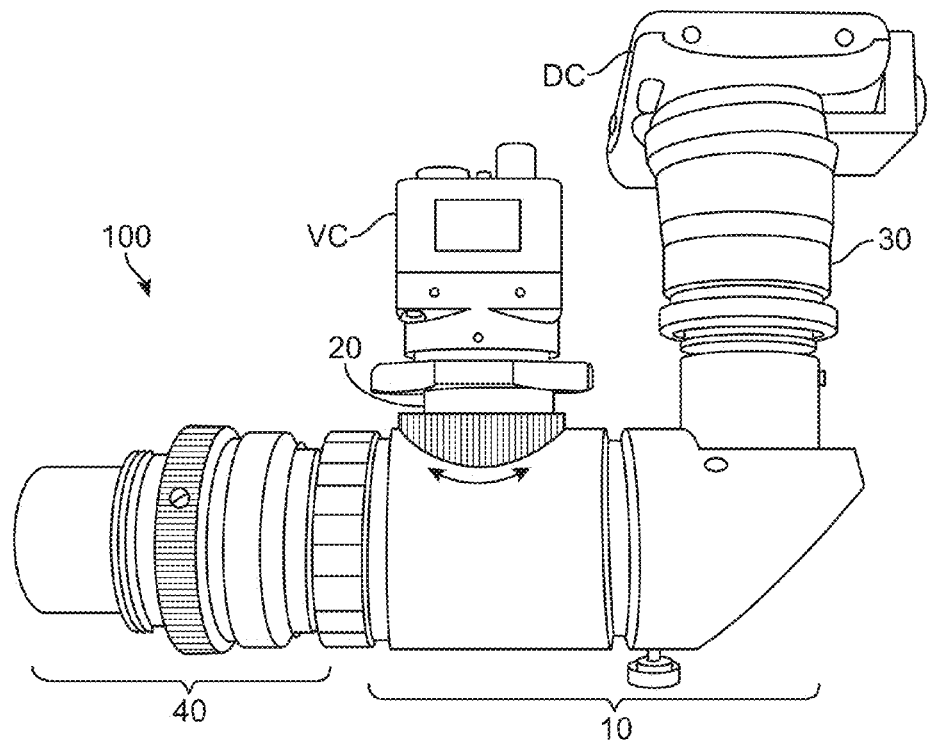

The optical mount 40 may also include an adjustable iris ring, which includes an iris adjustment ring 44 to increase the depth of focus. The adjustable iris ring 44 is positioned so as to adjust an amount of light that passes along optical path Li through the parfocal lens with zoom adjustment ring 46. The iris is adjusted using an adjustment ring which is connected to the iris by a conventional linkage assembly that can be adjusted by a user when mounted to the optical observation device OD while imaging with the video camera VC and the digital camera DC. Alternatively, the adjustable iris ring 44 may include a motorized iris control mechanism having an internal drive wheel (not illustrated) which engages and rotates the adjustment ring which controls the adjustable iris ring 44 (FIGS. 2 and 3). Suitable iris control and drive systems are illustrated in U.S. Pat. Nos. 3,820,882 and 4,300,167, the disclosures of which are incorporated herein by reference.

The video camera VC is mounted to the main body housing 10 with the video camera mount 20. The video camera mount 20 interfaces with the video camera VC so as to secure the video camera VC to the main body housing 10 aligned with the first optical path L1. In this embodiment, the video camera mount 20 includes a receptacle that receives a portion of the video camera VC and a locking ring 22 for securely attaching the video camera VC. The video camera mount 20 may also include a video image focusing assembly 26 having an auxiliary lens that allows a user to increase the zoom range to the video camera VC independent from the digital camera DC image. For example, an auxiliary fixed lens used in conjunction with a zoom lens having a zoom range of about 40 mm to 80 mm may increase the zoom range to a range from about 70 mm to 140 mm. A C-mount video image focusing assembly 26 is shown attached to the video camera VC in FIG. 2. The video camera mount 20 may also include a fine focus adjustment by which a user can further refine the focus of the video camera image during a procedure. Optionally, the video camera mount 20 adapter may further include a C-mount ring 24 that allows for a zoom range from 40 mm to 80 mm. The video camera mount 20 may be secured with a locking ring, such as that described in U.S. Pat. No. 5,264,928, that is adapted to receive a C-mount ring.

The digital camera DC is mounted to the main body housing with the digital camera mount 30. In this embodiment, the digital camera DC mounts to the main body 10 near the distal end of the main body housing 10 so as to allow digital imaging of light received along the second optical path L2. The digital camera mount typically includes a body 32 that includes a sleeve portion that receives the optical path L2 and prevents ambient light from entering the digital camera lens and an attachment portion that secures the digital camera DC in position relative to the sleeve portion of the digital camera mount 30, as shown in FIGS. 1-3.

In the embodiment of FIG. 2, the sleeve portion (the lower portion of digital camera mount body 32 as shown) is a hollow cylindrical body having a proximal end at which the digital camera mount 30 attaches to the main body housing 10 and a distal end near where the digital camera DC is secured. The sleeve portion is configured so as to allow full range of use of the extendable zoom lens of the digital camera (shown in dashed lines in FIG. 2). The sleeve portion typically extends a distance of about 1 cm to 2.5 cm, preferably about 2 cm from the camera face, and includes an axial passageway with a 10× eyepiece extending therethrough having a diameter of about 2.3 cm. The eyepiece of sleeve portion attaches to the rotatable portion 11 so that the axial passageway of the sleeve portion is substantially aligned with optical path L2. The rotatable portion 11 and/or sleeve portion may further include a centering mechanism 14 to center and facilitate alignment of a moveable portion that interfaces with the sleeve (and digital camera mounted thereon) with optical path L2. The centering mechanism 14 may include a plurality of screws that extend inwardly toward optical path L2, for example three centering screws spaced 120 degrees apart around the circumference of the opening, so that a user may center the sleeve along optical path L2 by screwing one or more of the screws while the proximal portion of the sleeve 32 is secured within the movable portion disposed within rotatable portion 11.

In the embodiment of FIG. 2, the attachment portion (the upper portion of the digital camera mount body 32 as shown) is a C-clamp shaped portion adjacent the distal end of the sleeve portion. The C-clamp attachment portion is configured to interface with a base of the digital camera DC to secure the digital camera DC relative to sleeve portion for imaging of light directed along the optical path L2. Typically, the C-clamp attachment portion includes a mounting screw 35 that fits into a standard tripod mount receptacle 36 of any standard, off-the-shelf digital camera DC so that when the digital camera DC is placed within the C-clamp (as shown by the dotted lines in FIG. 2) the C-clamp portion securely attaches the digital camera DC to the sleeve 32. The C-clamp is dimensioned so as to receive any of a plurality of digital cameras of differing types and brands. For example, by use of the mounting screw 35, the digital camera mount 30 can secure digital cameras having bases of varying thickness and width so long as the extendable zoom lens of the digital camera DC extends at least partially through the sleeve portion when mounted to the digital camera mount 30.

Figure 6:
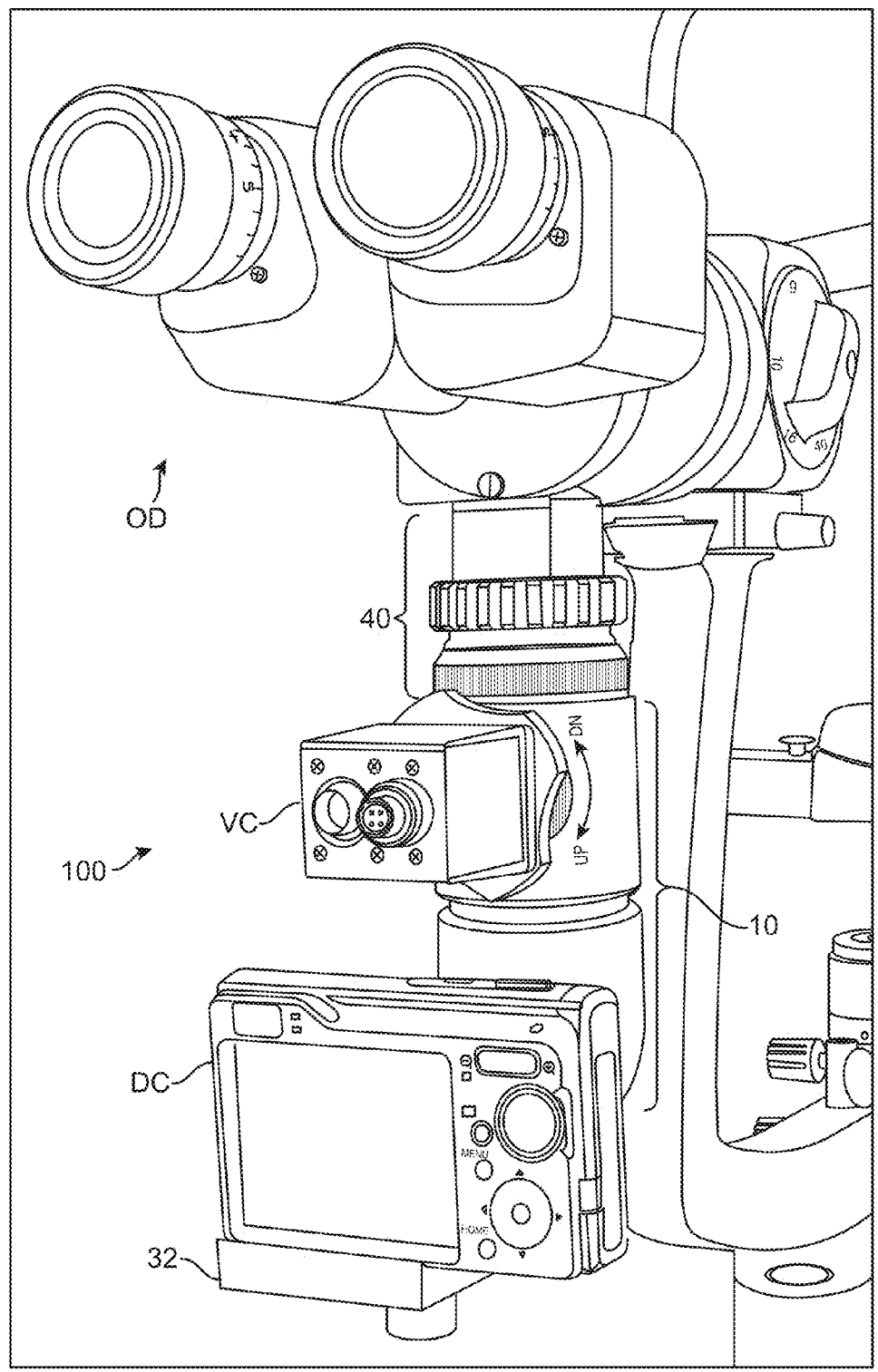
FIG. 6 shows the example universal adapter system of FIG. 1 having a video camera and digital camera mounted thereon.

In an example embodiment, the main body housing 10 includes a rotatable portion 11 that rotates about an axis of optical path Li and further includes a reflective surface 13, such as a prism or mirror, that directs light along optical path L2 in a direction transverse to optical path Li. Typically, the rotatable portion 11 can be rotated by 360 degrees about the optical path L2 and reflects the second optical path L2 at an angle of about 90 degrees relative the input image path Li. A user may rotate the rotatable portion 11 as needed during an imaging procedure, even when the digital camera DC is mounted thereon. This configuration advantageously allows for greater adaptability and accessibility of the digital camera by a user of the optical observation device OD. For example, as shown in FIG. 6, the digital camera can be positioned below the eyepieces of the optical observation device OD thereby allowing a primary user viewing an image with the optical observation device to simultaneously image with the digital camera DC. Alternatively, the rotatable portion 11 may be rotated, as shown in FIG. 1, to allow a secondary user to digitally image the view observed by the primary user operating the optical observation device OD. The rotatable portion 11 may be secured once rotated by the user to a desired position by adjusting locking device 15, the locking device typically including an inwardly extending screw that prevents inadvertent rotation during a procedure when extended.

In some embodiments, adapter 100 includes a lens assembly near the rotatable portion 11 and digital camera mount 30. As shown in FIG. 3, for example, the main body 10 and digital camera mount 30 may include lenses 17A and 17B disposed along optical path L2 so as to allow focus and/or magnification of the digital camera image, particularly when using the zoom feature of the digital camera. As shown in the FIG. 3, the lenses 17A and 17B are positioned along the optical path L2 on either side of reflective surface 13. Typically, lens 17A is an objective lens and 17B is an eyepiece lens that magnifies the image received from lens 17A and prism 13 may be configured to correct an orientation of the image so that the orientation of the digital camera DC image corresponds with an orientation of the video camera VC image.

The lenses 17A and 17B will be selected to be optically compatible with lens cartridge 42 disposed within the optical device mount 40. One particular advantage of this configuration is that it allows for use of the zoom feature of the digital camera at a variety of different focal length magnifications provided by adapter 100 (for example, as shown in FIG. 1). The present invention is particularly useful as the lenses associated with the lens cartridge can be selected or adjusted to simultaneously provide different focal length magnifications for each of the video camera VC and the digital camera DC, while the lenses disposed along optical path L1 may be adjusted to provide different focal lengths for the video camera VC independent of the digital camera DC and the digital camera DC zoom feature can be used to adjust zoom independent of the video camera VC.

Figure 7:
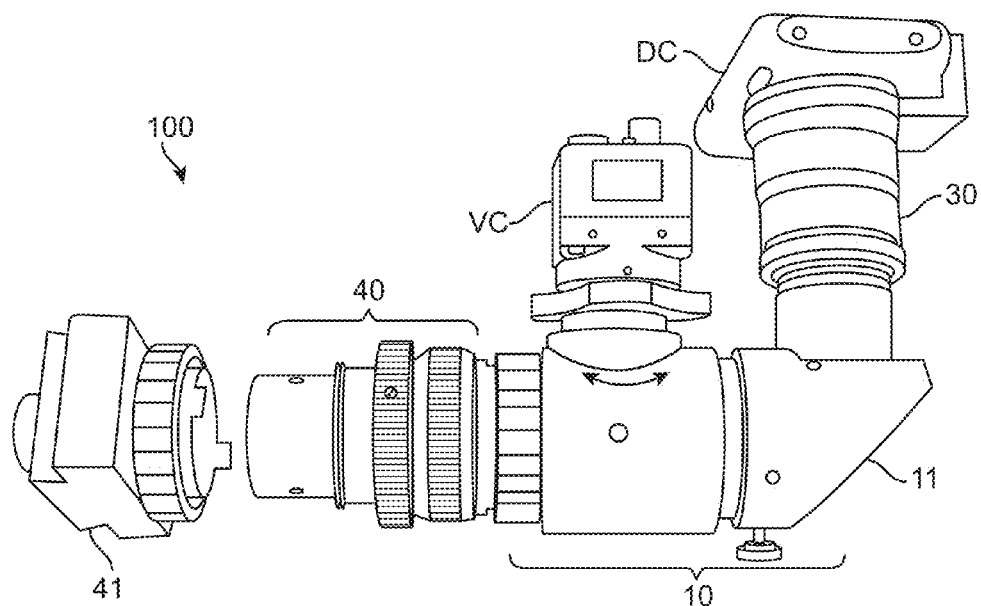
FIGS. 7 and 8 show the universal adapter system of FIG. 4 with an optical port converter before and after attachment of the converter to the adapter.
Figure 8:
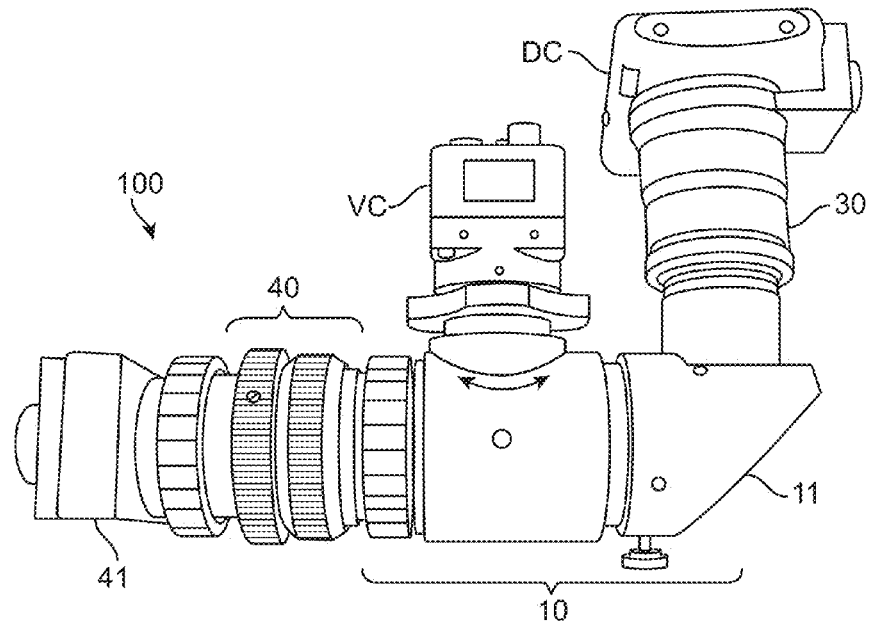

In another aspect, the optical mount 40 may include additional components to facilitate attachment of the adapter 100 to differing types of microscopes. For example, as shown in FIG. 1, the adapter 100 can be easily mounted to an auxiliary optical port AP of a Zeiss brand microscope. FIGS. 7 and 8 depict an optical port converter 41, shown before and after attachment, respectively. The port converter 41 shown facilitates mounting of the adapter 100 to an optical port of a Leica brand microscope; although a variety of port convertors compatible with differing types and brands of optical observation devices are well within the principles of the invention.

Figure 9:
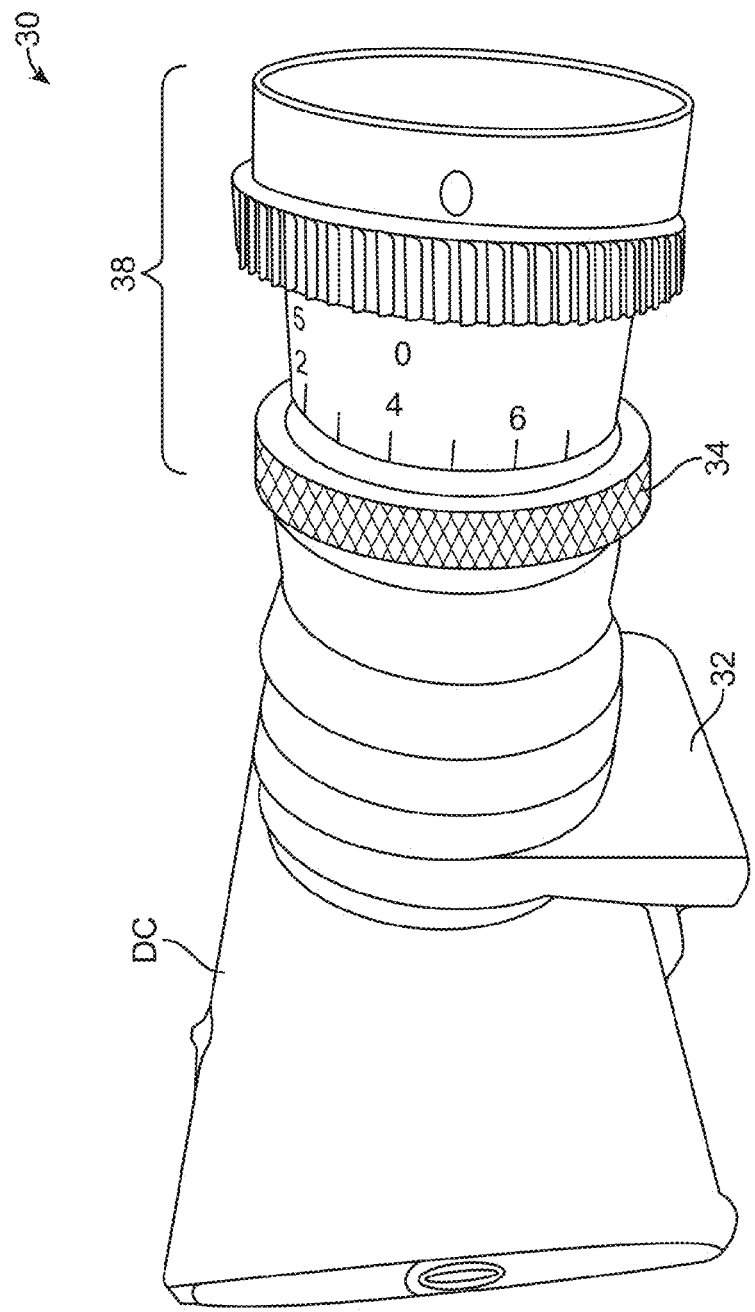
FIG. 9 shows a binocular tube interface adapter for use with a digital camera mount or various other adapter components.

In some embodiments, the digital camera mount 30 can be attached directly to a binocular tube of an optical device OD by use of a binocular tube interface 38. As shown in FIG. 9, the sleeve portion of the digital camera mount 30 interfaces with the binocular tube interface 38, which in turn, interfaces with the binocular tube of the optical viewing device, OD, such as a surgical microscope or ophthalmic slit lamp. The binocular tube interface 38 receives the eyepiece lens 17B of the digital camera mount 30. A user can attach the digital camera mount 30 of FIG. 9 to a binocular tube of an optical device OD by: removing the eyepiece from the binocular tube, slide the digital camera mount 30 with eyepiece lens 17B into the binocular tube interface 38 and secure the assembly to the binocular tube interface 38 using locking ring 34.

In some embodiments, a smartphone adapter 50 may be used to allow use of a smartphone having a video or still image capture feature with the above described universal adapter system. In such embodiments, the smartphone SM and smartphone adapter 50 may be used in place of the digital camera DC and digital camera mount 30. Alternatively, the smartphone adapter 50 may be used with an optical device OD as a separate adapter to allow imaging with the smartphone SM attached directly to the optical device OD or when used in conjunction with the binocular tube interface 38.

Figure 10A:
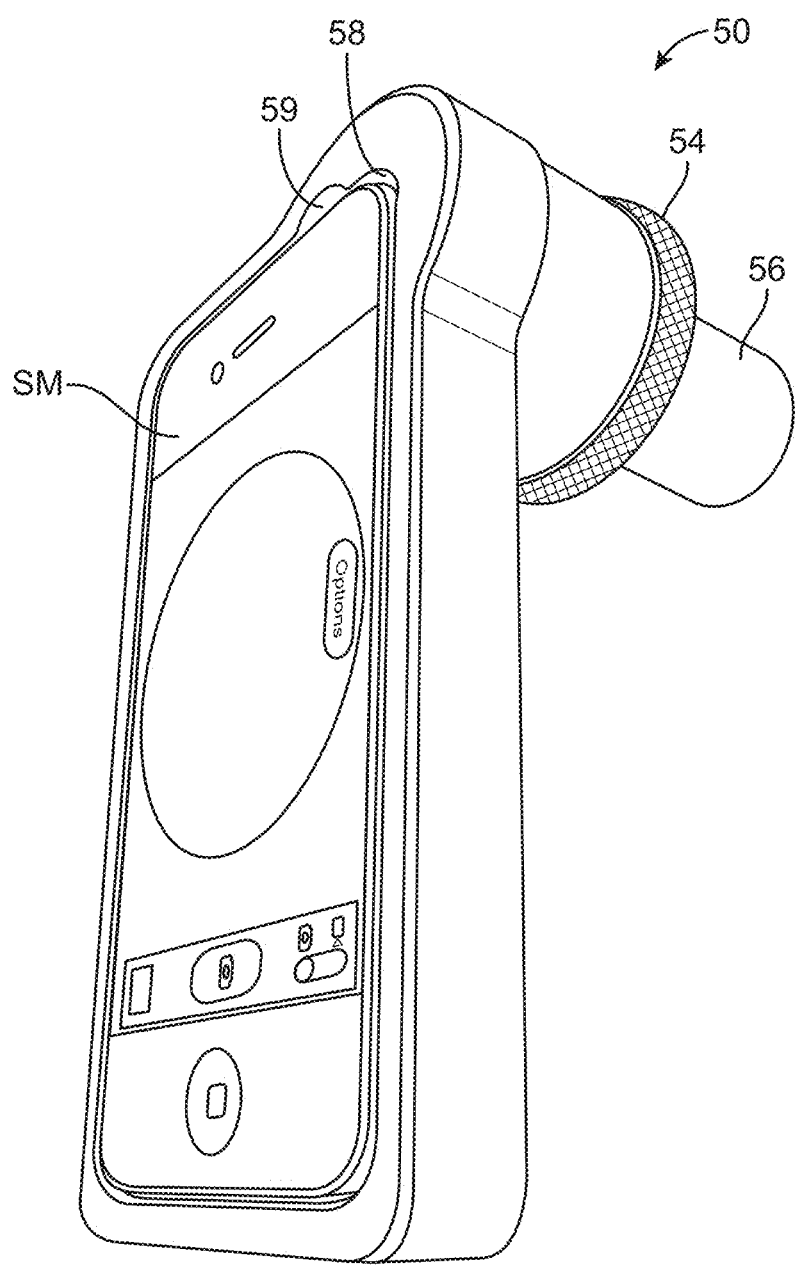
FIGS. 10A-10C show a smartphone adapter for use with a universal adapter system or for use as a separate adapter.
Figure 10B:
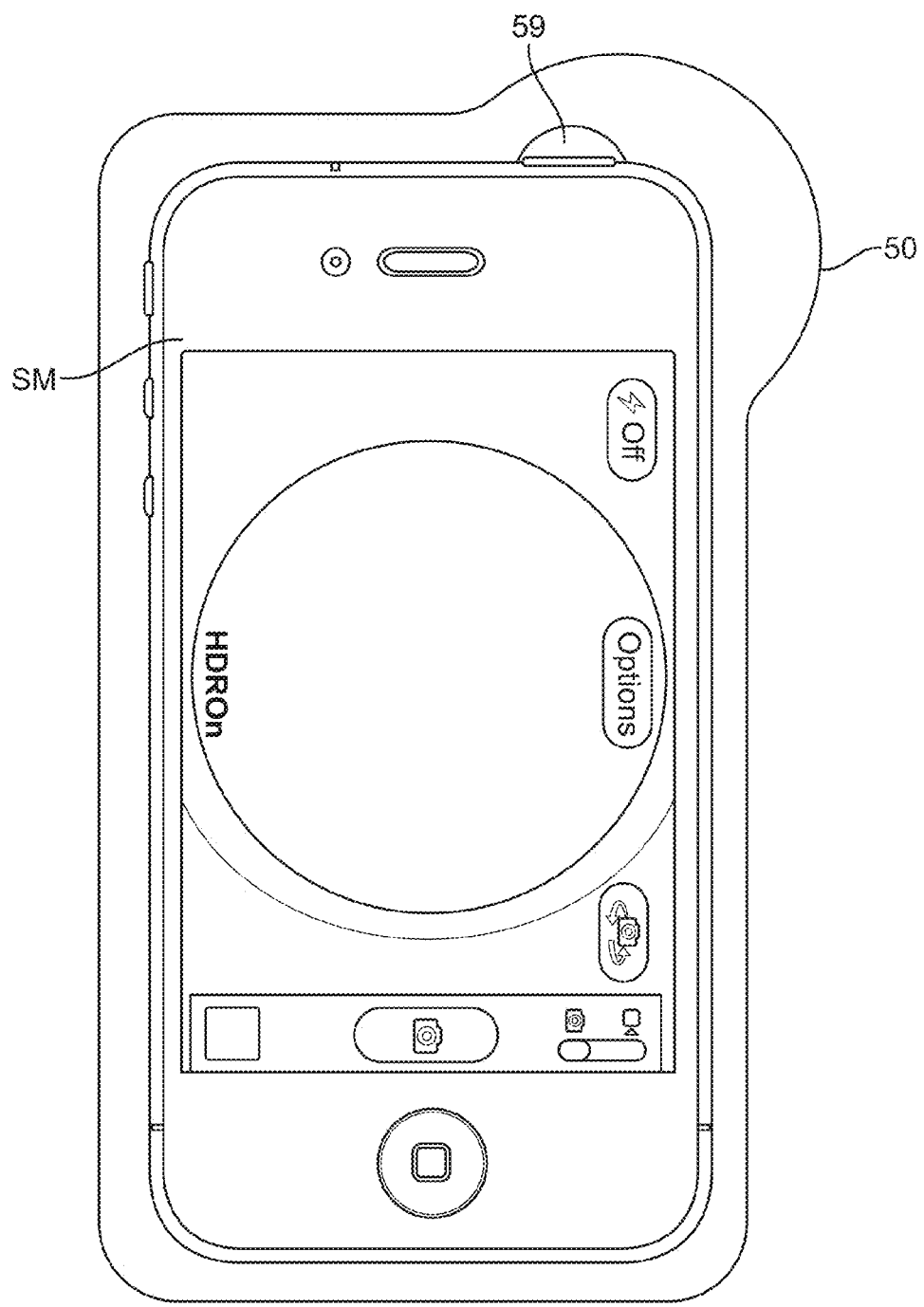
Figure 10C:
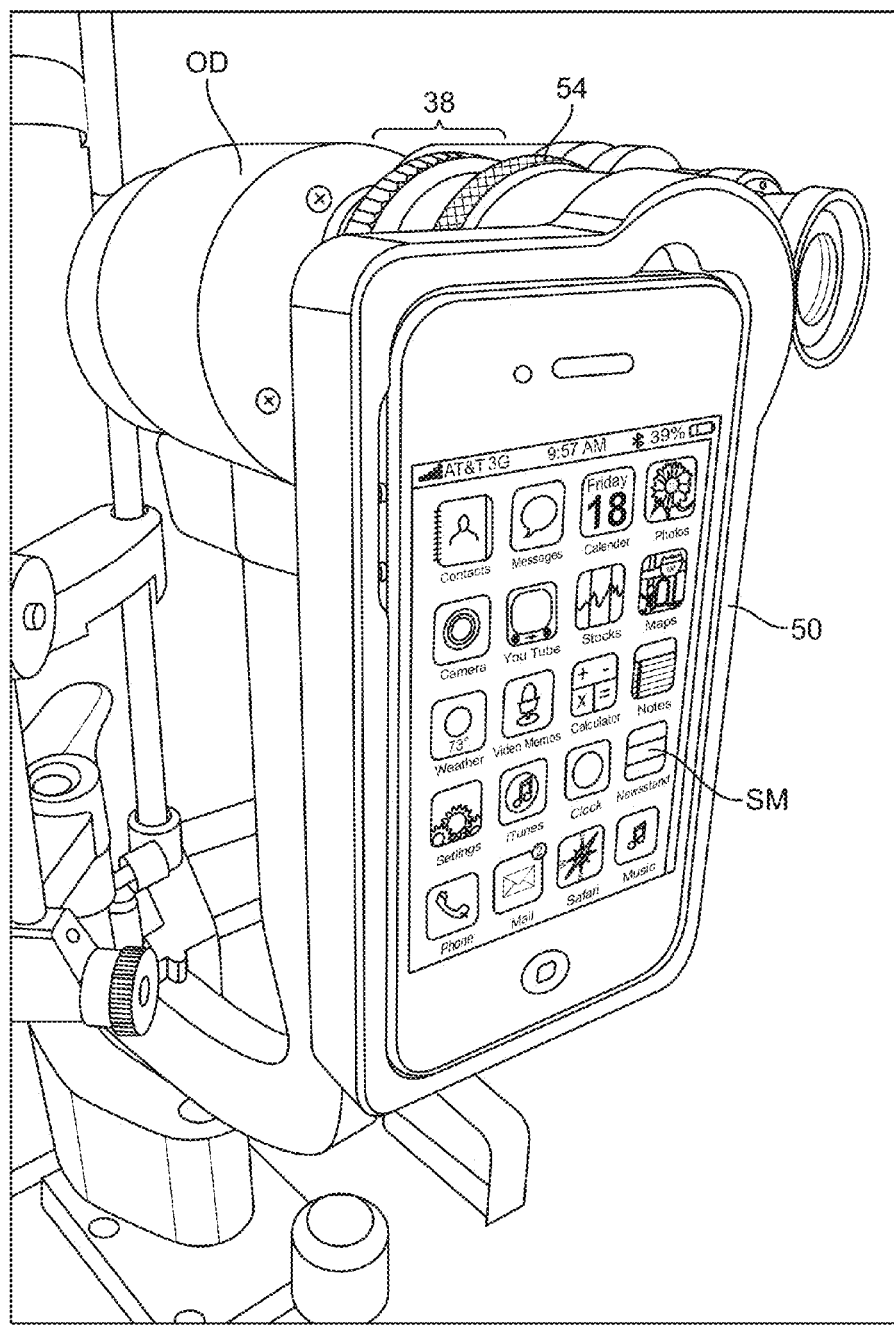

An example of a smartphone adapter 50 is shown in FIGS. 10A-10C. FIG. 10 shows a smartphone adapter 50 having a smartphone SM disposed within a recess 58 configured to fittingly receive a standard sized smartphone SM, such as an iPhone™, so that the smartphone can remain securely positioned within the recess, such as in a friction fit, without requiring an additional rigid mechanical fastening means to secure the device in place. The recess allows substantially the entire front surface of the smartphone to remain accessible to allow the various functions of the device to be accessed by a user while the smartphone MS is secured within the recess. The recess 58 may include a removal feature 59 to allow a user to easily remove the smartphone SM once fittingly received within the recess 58. As shown in FIGS. 10A and 10B, the removal feature 59 includes a semi-circle shaped recess that allows a user to insert a fingertip on a side of the smartphone SM to exert an outward force to remove the smartphone SM from the recess. The recess 58 may also include a finger hole extending through the underside of the adapter 50 near a center of the recess 58 so that a user can insert a finger to remove the smartphone from the adapter 50. It is appreciated that the removal feature 59 may include a variety of other features to allow for easy removal of the device, such as a button or lever to allow the user to exert an outward force on the smartphone device to facilitate removal of the smartphone device.

The smartphone adapter may include cylindrical sleeves portion that extends to a cylindrical eyepiece optic 56 that includes a lens, such as eyepiece lens 17B, and may optionally include additional adjustable lenses or focus adjustments. The cylindrical sleeve also surrounds an optical path extending from the camera lens disposed on the backside of the smartphone device SM, thereby preventing bleeding of ambient light into the optical path and ensuring sufficient light is captured by the lens of the smartphone SM to provide a high quality image. When fastened to the binocular tube interface 38, such as by tightening a locking ring 54, the cylindrical sleeve 56 extends into the binocular tube interface 38 to prevent ambient light from entering the optical path to maintain a high quality image. A similar procedure as described above in reference to the digital camera mount 30 may be used to attach and secure the smartphone adapter 50, sliding the eyepiece optic 17B and cylindrical sleeve 56 into the binocular tube interface 38 and securing the assembly using locking ring 54.

In some embodiments, the smartphone adapter 50 may be used to attach a smartphone SM directly to a binocular tube of the optical observation device OD. FIG. 10C shows a smartphone disposed within a smartphone adapter 50 connected to a binocular tube of an optical device OD using a binocular tube interface 38, such as that described above.

Figure 11:
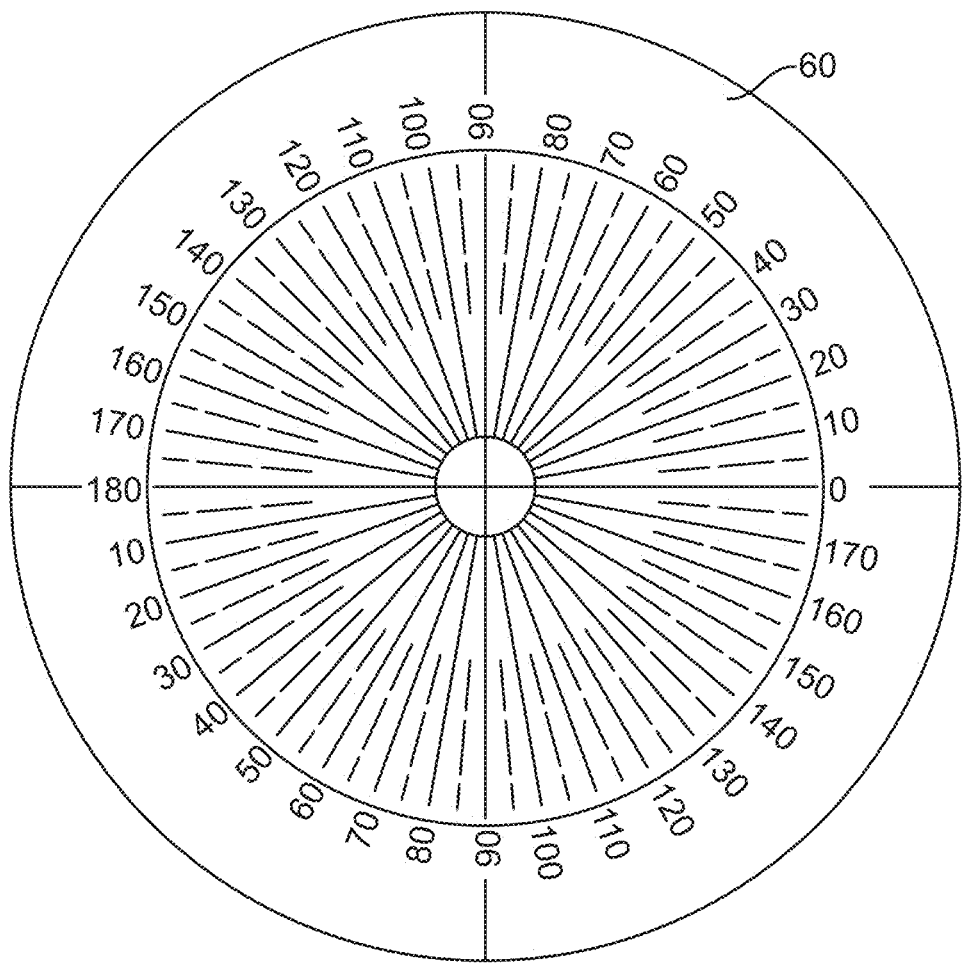
FIG. 11 shows an example Toric reticule for use with a digital camera adapter or smartphone adapter.
Figure 12:
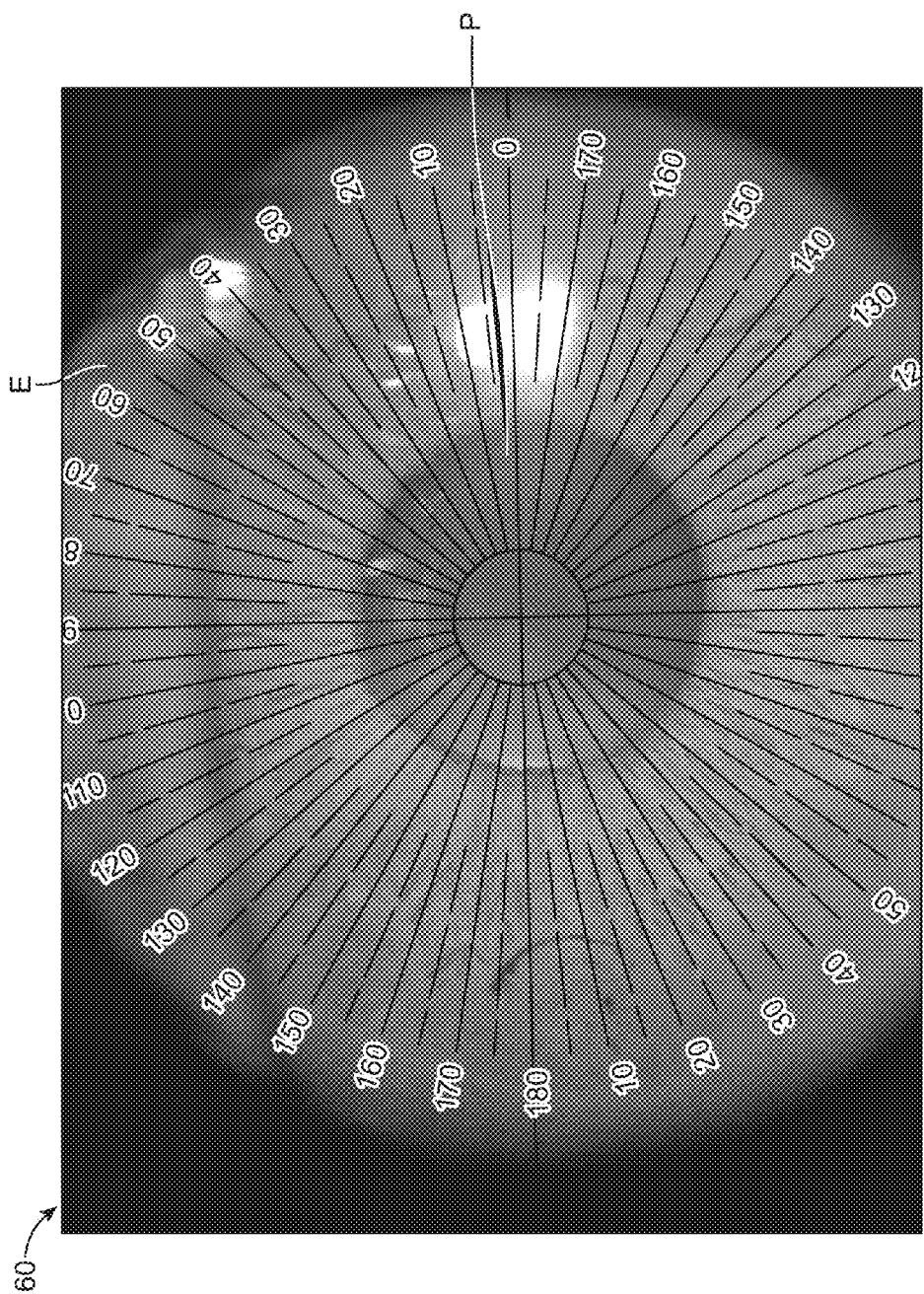
FIG. 12 shows an example documentation image taken using an adapter having a Toric reticule.

In one aspect, a universal adapter may include a Toric reticule 60, such as that shown in FIG. 11, the reticule designed to fit within the lens or eyepiece optic 17B of the digital camera mount 30. Typically, the Toric reticule is disposed within the digital camera mount 30 or smartphone adapter 50 so that the measurement markings of the Toric reticule appear in an image captured by the digital camera or smartphone device. An adapter configured to include a Toric reticule is particularly advantageous as it allows a user to document the positioning of a Toric intraocular lens (IOL) designed to correct astigmatism. When implanting a Toric IOL, such as in a cataract surgical procedure, the IOL must be precisely positioned. By using an adapter having a Toric reticule disposed within the optical path of the digital camera, a user can locate/measure the astigmatism of an eye during a pre-operative exam and document how the Toric IOL should be positioned during surgery by imaging the eye through the reticule in the adapter. An example of an image of the eye taken using such an adapter is shown in FIG. 12, the pupil P of the eye E clearly visible through the measured markings of the Toric reticule 60. After the IOL is inserted into the anterior chamber, it is rotated to the documented pre-operative position and a second image may be taken using the adapter to confirm that the IOL is in the proper position. During surgery, the camera mount 30 with Toric reticule 60 and digital camera DC can be attached to the universal adaptor 100 to document the final position of the Toric IOL. Thus, the above described adapter allows for more precise placement of the IOL, thereby improving accuracy and predictability of surgical outcomes.

Figure 13A:
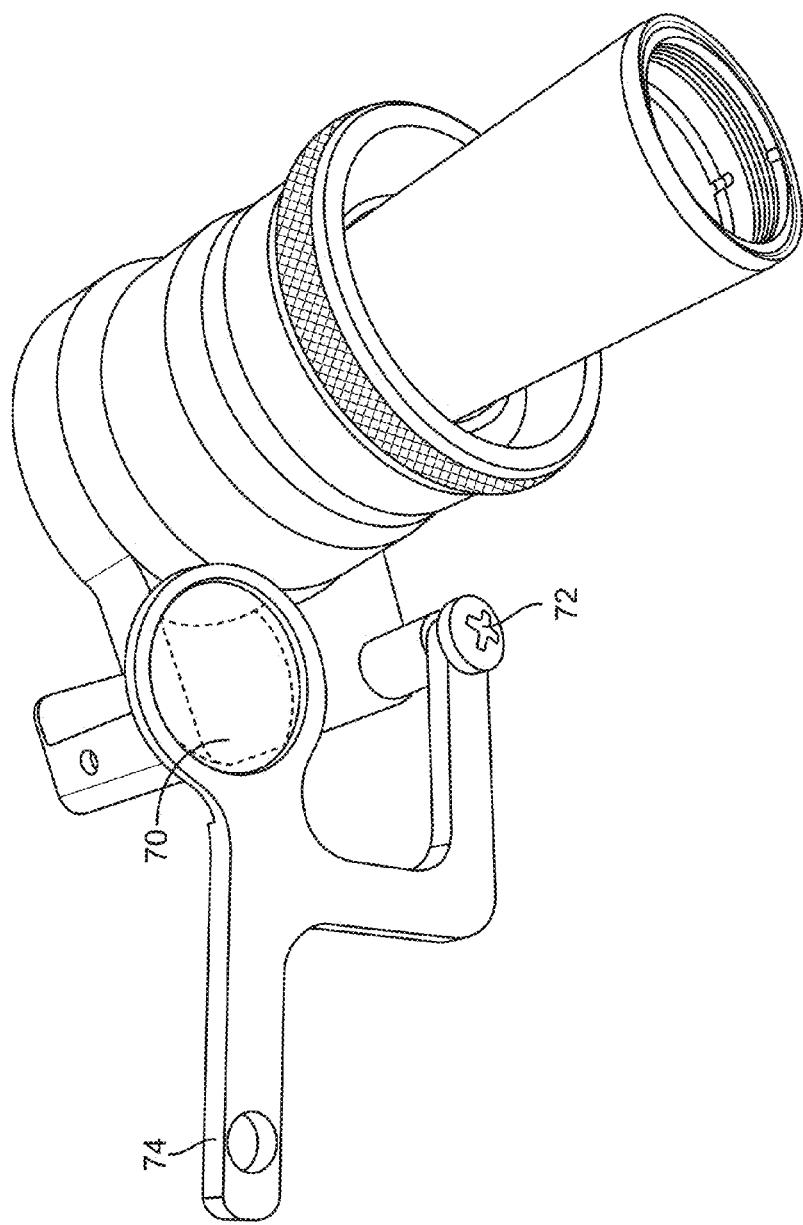
FIG. 13A shows an example light filter for use with a digital camera adapter or smartphone adapter.
Figure 13B:
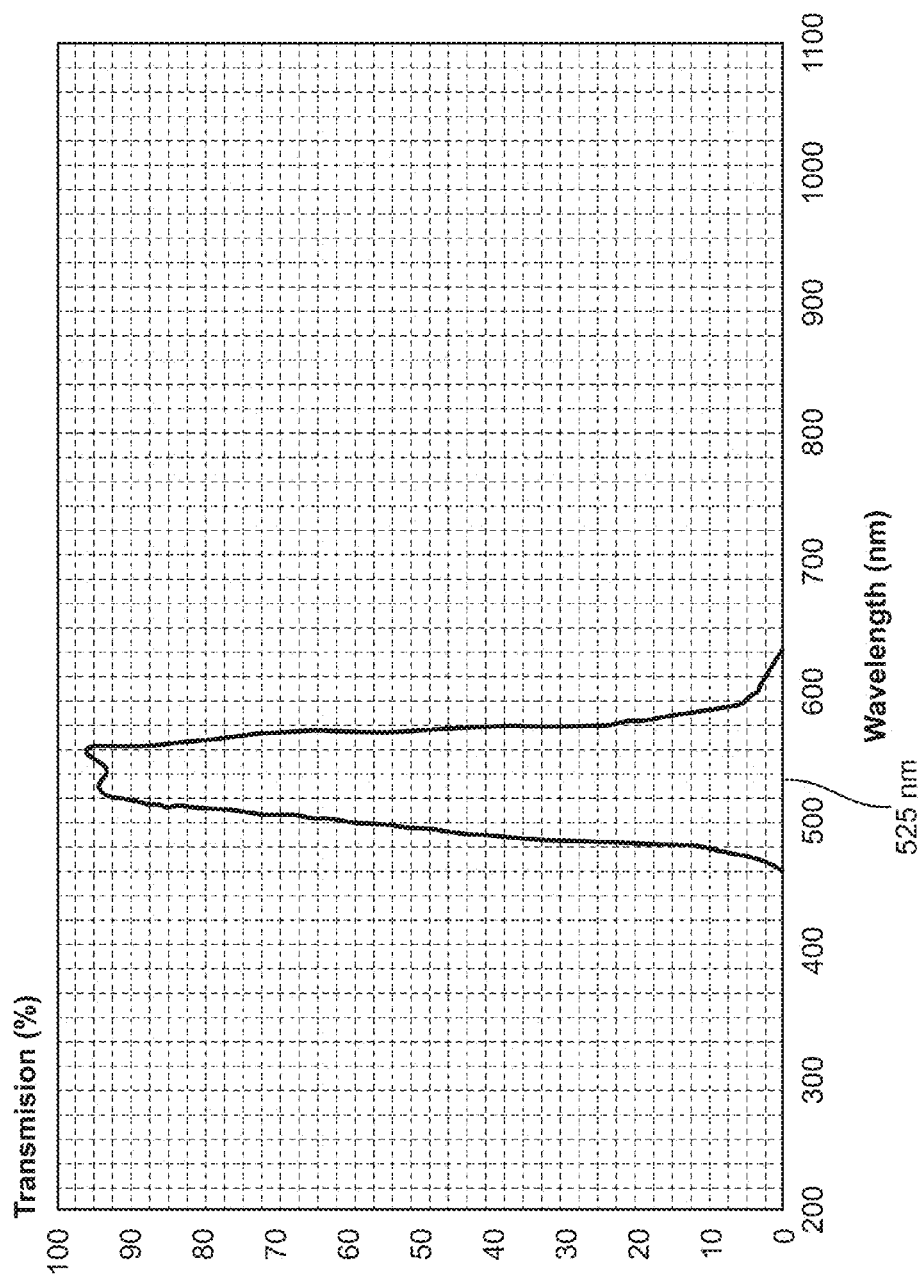
FIG. 13B shows a transmission graph of an example yellow light filter.
Figure 14:
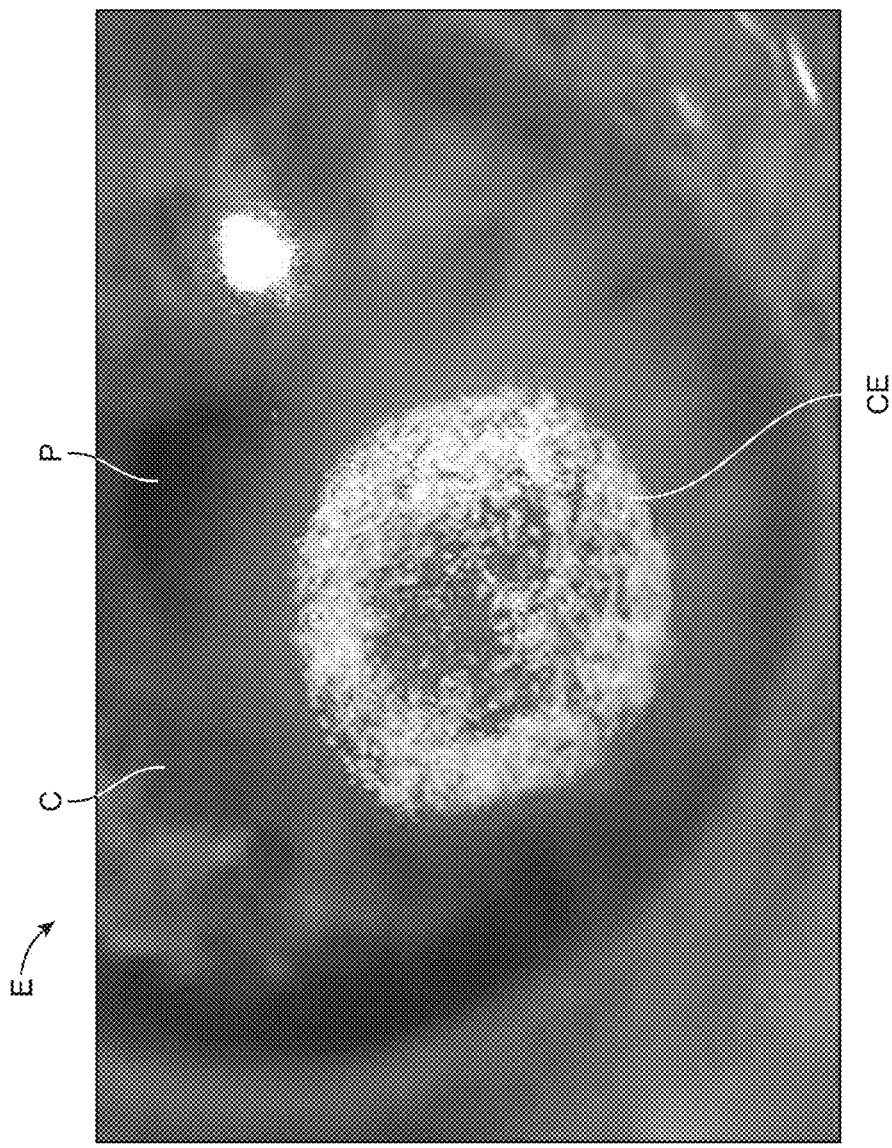
FIG. 14 shows an example documentation image of a corneal ulcer taken using an adapter with a light filter.

In another aspect, the adapter may include a movable light filter 70 that can be easily inserted into or removed from an imaging optical path within the adapter. The light filter 70 may filter out light of a particular wavelength or range of wavelengths to enhance visibility of various features under certain conditions. An example of a digital camera adapter having a movable light filter 70 is shown in FIG. 13A. For example, the light filter may comprise a yellow filter 70 allowing transmission of wavelengths of about 525 nm, such that when used in conjunction with fluorescein dye on the cornea that is excited by cobalt blue light emitted by a slit lamp, the yellow filter acting as a barrier filter substantially blocking wavelengths below 475 nm and wavelengths above 620 nm. A transmission graph of an example yellow filter is shown in FIG. 13B. Using an adapter having such a light filter allows for improved detection and document of corneal defects and diseases by the digital camera. An example image documenting the position and size of a corneal ulcer using such an adapter is shown in FIG. 14, the corneal ulcer CE on cornea C clearly visible below the pupil P of the eye E. This feature may also be used to provide improved documentation in a contact lens fitting or to provide high contrast imaging for various purposes.

The light filter may be attached in various location so as to be positionable within the optical path extending to the digital camera. Typically, the light filter is integrated with the digital camera mount 30, the smartphone adapter 50. Alternatively, the light filter may be included as an additional attachment or removable feature that interfaces with any of these components. The light filter may be inserted into or removed from the optical imaging path by flipping the filter in and out of the optical path. As shown in the example of FIG. 13A, the light filter may be attached to the adapter at a pivotal coupling 72 (e.g. an axel defined by a screw) such that the filter can be inserted and/or removed by manually moving lever 74. Once the light filter is within the proper position, the light filter may be locked in place either by tightening a screw defining the pivotal coupling 72. It is appreciated that various means may be used to secure the light filter into place during imaging through the filter.

Although the foregoing invention has been described in detail for purposes of clarity of understanding, it will be obvious that certain modifications may be practiced within the scope of the appended claims. For example, various features of the embodiments described herein may be combined and/or modified within an adapter or its associated components and remain within the spirit and scope of the invention.

What is claimed is:

1. An adapter system for mounting both a video camera and a digital camera on an optical observation device, said adapter system comprising:

a main body including a housing and an internal beam splitter oriented to receive light along an axial input image path and to direct (1) a first portion of the light along a first optical path, the first optical path being at an angle to the axial input image path, and (2) a second portion of the light along a second optical path, the second optical path being at an angle to the first optical path:

an optical device mount on the main body housing, the optical device mount having an entrance end configured to attach to an optical port of the optical observation device such that, when attached, light passes through the entrance end and enters the main body housing along the input image path through the optical device mount;

a lens assembly disposed along the axial input image path between the entrance end and the internal beam splitter:

the lens assembly comprising a parfocal optical zoom:

a video camera mount on the main body housing, the video camera mount being configured to attach to the video camera such that, when attached, the video camera is optically coupled to the first optical path; and a digital camera mount on the main body housing, the digital camera mount being configured to attach to the digital camera such that, when attached, the digital camera is optically coupled with the second optical path;

wherein, when attached, the video camera and digital camera are optically coupled with the first and second optical paths so as to allow for simultaneous video imaging with the video camera and digital imaging with the digital camera of an image from the optical observation device, wherein at least one of the video camera mount and the digital camera mount is configured to attach to a smart phone having an image capture feature.

2. An adapter system for mounting both a video camera and a digital camera on an optical observation device, the optical observation device comprising a surgical microscope or an ophthalmic slit lamp, said adapter system comprising:

a main body including a housing and an internal beam splitter oriented to receive light along an axial input image path and to direct (1) a first portion of the light along a first optical path, the first optical path being at an angle to the axial input image path, and (2) a second portion of the light along a second optical path, the second optical path being at an angle to the first optical path:

an optical device mount on the main body housing, the optical device mount having an entrance end configured to attach to an optical port, of the optical observation device such that, when attached, light passes through the entrance end and enters the main body housing along the input image path through the optical device mount:

a lens assembly disposed along the axial input image path between the entrance end and the internal beam splitter:

a video camera mount on the main body housing, the video camera mount being configured to attach to the video camera such that, when attached, the video camera is optically coupled to the first optical path;

a digital camera mount on the main body housing, the digital camera mount being configured to attach to the digital camera such that when attached, the digital camera is optically coupled with the second optical path: and the digital camera mount, and the video camera mount being detachable from the main body housing;

wherein, when attached, the video camera and digital camera are optically coupled with the first and second optical paths so as to allow for simultaneous video imaging with the video camera and digital imaging with the digital camera of an image from the optical observation device, wherein at least one of the video camera mount and the digital camera mount is configured to attach to a smart phone having an image capture feature.

3. The adapter system of claim 1, wherein the parfocal optical zoom has a range of focal lengths from at least about 40 mm to about 80 mm.

4. The adapter system of claim 1, further comprising an adjustable iris having an adjustable aperture, the adjustable iris positioned along the axial input image path such that light passes through the adjustable aperture before passing through the parfocal optical zoom.

5. An adapter system for mounting both a video camera and a digital camera on an optical observation device, said adapter system comprising:

a main body including a housing and an internal beam splitter oriented to receive light along an axial input image path and to direct (Da first portion of the light along a first optical path, the first optical path being at an angle to the axial input image path, and (2) a second portion of the light along a second optical path, the second optical path being at an angle to the first optical path:

an optical device mount on the main body housing, the optical device mount having an entrance end configured to attach to an optical port of the optical observation device such that, when attached, light passes through the entrance end and enters the main body housing along the input image path through the optical device mount:

a lens assembly disposed along the axial input image path between the entrance end and the internal beam splitter;

a video camera mount on the main body housing, the video camera mount being configured to attach to the video camera such that, when attached, the video camera is optically coupled to the first optical path; and a digital camera mount, on the main body housing, the digital camera mount, being configured to attach to the digital camera such that, when attached, the digital camera is optically coupled with the second optical path:

wherein, when attached, the video camera and digital camera are optically coupled with the first and second optical paths so as to allow for simultaneous video imaging with the video camera and digital imaging with the digital camera of an image from the optical observation device;

a set of interchangeable lenses of differing fixed focal lengths, and wherein the lens assembly includes a said interchangeable lens, whereby a user can adjust the focal length by the choice of the interchangeable lens from the set of interchangeable lenses, wherein at least one of the video camera mount and the digital camera mount is configured to attach to a smart phone having an image capture feature.

6. The adapter system 5, wherein the set of interchangeable lenses of differing fixed focal lengths include fixed focal lengths lenses of F55, F65, F85, F107 and F135, respectively.

7. The adapter system of claim 1, wherein the internal beam splitter directs a greater portion of the light along the first optical path than the second path.

8. The adapter system of claim 7, wherein the internal beam splitter splits the light from the axial input image path between the first and second paths at a ratio of about 70/30.

9. The adapter system of claim 1, wherein the internal beam splitter splits roughly equal portions of the light from the axial input image path between the first and second paths.

10. An adapter system for mounting both a video camera and a digital camera on an optical observation device, said adapter system comprising:

a main body including a housing and an internal beam splitter oriented to receive light along an axial input, image path and to direct (1) a first portion of the light along a first optical path, the first, optical path being at an angle to the axial input image path, and (2) a second portion of the light along a second optical path, the second optical path being at an angle to the first optical path;

an optical device mount on the main body housing, the optical device mount having an entrance end configured to attach to an optical port of the optical observation device such that, when attached, light passes through the entrance end and enters the main body housing along the input image path through the optical device mount:

a lens assembly disposed along the axial input, image path between the entrance end and the internal beam splitter;

a video camera mount on the main body housing, the video camera mount being configured to attach to the video camera such that, when attached, the video camera is optically coupled to the first optical path;

a digital camera mount on the main body housing, the digital camera mount being configured to attach to the digital camera such that, when attached, the digital camera is optically coupled with the second optical path, the digital camera comprising an objective zoom lens: and the digital camera mount being configured to fixedly attach to a base of the digital camera and is configured to allow movement of the objective zoom lens of the digital camera along the second optical path;

wherein, when attached, the video camera and digital camera are optically coupled with the first and second optical paths so as to allow for simultaneous video imaging with the video camera and digital imaging with the digital camera of an image from the optical observation device, wherein at least one of the video camera mount and the digital camera mount is configured to attach to a smart phone having an image capture feature.

11. The adapter system of claim 10, wherein the digital camera mount includes a C-clamp for fixedly attaching to the base of the digital camera and a passage extending therethrough and through which the objective zoom lens of the digital camera can extend while the digital camera is fixedly attached to the C-clamp.

12. The adapter system of claim 10, wherein the main body housing includes a rotatable portion that attaches to the digital camera mount, the rotatable portion including a reflective surface for directing a portion of the second path along a direction transverse to the axial input image path and through the digital camera mount.

13. The adapter system of claim 11, wherein the digital camera mount comprises an open-ended, hollow cylindrical member, the C-clamp being disposed near one end of the cylindrical member, while the opposite end is attached to the main body housing.

14. The adapter system of claim 11, wherein the C-clamp includes a screw for engaging with a tripod mount in the base of the digital camera.

15. The adapter system of claim 10, further comprising a centration feature for centering the digital camera mount on a center of the second optical path.

16. The adapter system of claim 15, wherein the centration feature comprises a portion of the main body housing having a plurality of screws surrounding and extending inwardly toward the second optical path extending therethrough, such that a user may adjust one or more screws in the plurality when the digital camera mount is positioned therein so as to center the digital camera mount on the second optical path.

17. The adapter system of claim 10, wherein the adapter system includes two lenses positioned along the second optical path so as to focus and/or magnify an image of the second optical path for imaging with the digital camera.

18. The adapter system of claim 17, wherein the adapter system includes a reflective surface disposed along the second optical path between the two lenses so as to correct an orientation of the image of the second optical path for imaging with the digital camera.

19. The adapter system of claim 10, wherein the digital camera mount is attachable to any of a plurality of differing types or brands of digital cameras.

20. The adapter system of claim 1, wherein the video camera mount includes an interface for fixedly securing the video camera to the adapter in alignment with the first optical path, the first optical path extending through an aperture of the video camera mount.

21. The adapter system of claim 20, wherein the interface includes a threaded opening.

22. An adapter system for mounting both a video camera and a digital camera on an optical observation device, said adapter system comprising:

a main body including a housing and an internal beam splitter oriented to receive light along an axial input image path and to direct (1) a first portion of the light along a first optical path, the first optical path being at an angle to the axial input image path, and (2) a second portion of the light along a second optical path, the second optical path being at an angle to the first optical path:

an optical device mount on the main body housing, the optical device mount having an entrance end configured to attach to an optical port of the optical observation device such that, when attached, light passes through the entrance end and enters the main body housing along the input image path through the optical device mount:

a lens assembly disposed along the axial input, image path between the entrance end and the internal beam splitter;

a video camera mount on the main body housing, the video camera mount being configured to attach to the video camera such that, when attached, the video camera is optically coupled to the first optical path;

the video camera mount includes an interface for fixedly securing the video camera to the adapter in alignment with the first optical path, the first optical path extending through an aperture of the video camera mount;

a digital camera mount on the main body housing, the digital camera mount being configured to attach to the digital camera such that, when attached, the digital camera is optically coupled with the second optical path: and an auxiliary lens positioned along the first optical path that when used in conjunction with a zoom lens increases the zoom range while video imaging with the video camera;

wherein, when attached, the video camera and digital camera are optically coupled with the first and second optical paths so as to allow for simultaneous video imagine with the video camera and digital imaging with the digital camera of an image from the optical observation device, wherein at least one of the video camera mount and the digital camera mount is configured to attach to a smart phone having an image capture feature.

23. The adapter system of claim 22, wherein when the zoom range of the zoom lens is about 40 mm to 80 mm, the auxiliary lens provides an increased zoom range of about 70 mm to about 140 mm.

24. The adapter system of claim 22, further comprising a fine focus adjustment disposed within the first optical path so as to allow the user to adjust focus during video imaging.

25. The adapter system of claim 20, wherein the video camera mount is attachable to any of a plurality of differing types or brands of video cameras.

26. The adapter system of claim 1, wherein the optical device mount is attachable to any of a plurality of differing types or brands of optical observation devices.

27. The adapter system of claim 26, wherein the plurality of different types of optical observation devices include differing brands of surgical microscopes and ophthalmic slit lamps using mechanical beam splitters.

28. The adapter system of claim 27, wherein the optical device mount includes one or more detachable portions corresponding to at least one particular type or brand of optical observation device.

29. An adapter system for mounting both a video camera and a digital camera on an optical observation device, said adapter system comprising:
  a main body including a housing and an internal beam splitter oriented to receive light along an axial input image path and to direct (1) a first portion of the light along a first optical path, the first optical path being at an angle to the axial input image path, and (2) a second portion of the light along a second optical path, the second optical path being at an angle to the first optical path;
  an optical device mount on the main body housing, the optical device mount having an entrance end configured to attach to an optical port of the optical observation device such that, when attached, light passes through the entrance end and enters the main body housing along the input image path through the optical device mount;
  a lens assembly disposed along the axial input image path between the entrance end and the internal beam splitter;
  a video camera mount on the main body housing, the video camera mount being configured to attach to the video camera such that, when attached, the video camera is optically coupled to the first optical path; and
  a digital camera mount on the main body housing, the digital camera mount being configured to attach to the digital camera such that, when attached, the digital camera is optically coupled with the second optical path; and
  the digital camera mount comprising a smartphone adapter having a recess configured to fittingly receive a smartphone and a cylindrical sleeve defining an axial passageway along the second optical path, wherein the axial passageway extends from a location in the recess is aligned with a camera disposed on an underside of the smartphone when secured within the recess;
  wherein, when attached, the video camera and digital camera are optically coupled with the first and second optical paths so as to allow for simultaneous video imaging with the video camera and digital imaging with the digital camera of an image from the optical observation device.

30. The adapter system of claim 29, wherein the sleeve includes an adjustable locking ring disposed a distance away from the recess in which the smartphone is received, the locking ring configured to secure the smartphone adapter to the main body of the adapter.

31. The adapter system of claim 1 further comprising: a light filter positionable within the second optical path extending through the adapter system to the digital camera.

32. The adapter system of claim 31, wherein the light filter is integrated with the digital camera mount.

33. The adapter system of claim 31, wherein the light filter is pivotally coupled to the adapter so that the light filter is movable relative to the second optical path to allow a user to selectively pivot the light filter into or out of the second optical path as desired.

34. The adapter system of claim 31, wherein the light filter is a yellow light filter that filters certain wavelengths of light including wavelengths of about 525 nm.

35. An adapter system for mounting both a video camera and a digital camera on an optical observation device, said adapter system comprising:
  a main body including a housing and an internal beam splitter oriented to receive light along an axial input image path and to direct (1) a first portion of the light along a first optical path, the first optical path being at an angle to the axial input image path, and (2) a second portion of the light along a second optical path, the second optical path being at an angle to the first optical path:
  an optical device mount on the main body housing, the optical device mount having an entrance end configured to attach to an optical port of the optical observation device such that, when attached, light passes through the entrance end and enters the main body housing along the input image path through the optical device mount:
  a lens assembly disposed along the axial input, image path between the entrance end and the internal beam splitter;
  a video camera mount on the main body housing, the video camera mount being configured to attach to the video camera such that, when attached, the video camera is optically coupled to the first optical path; and
  a digital camera mount on the main body housing, the digital camera mount being configured to attach to the digital camera such that, when attached, the digital camera is optically coupled with the second optical path: and
  a Toric reticule disposed within the second optical path coupled with the digital camera to allow documentation imaging of the eye through the Toric reticule;
  wherein, when attached, the video camera and digital camera are optically coupled with the first and second optical paths so as to allow for simultaneous video imaging with the video camera and digital imagine with the digital camera of an image from the optical observation device,
  wherein at least one of the video camera mount and the digital camera mount is configured to attach to a smart phone having an image capture feature.

36. The adapter system of claim 35 wherein the Toric reticule is attached to the digital camera mount and positionable within the second optical path.

* * * * *